United States Patent
Kase

(10) Patent No.: US 12,357,338 B2
(45) Date of Patent: Jul. 15, 2025

(54) ULTRASONIC TREATMENT TOOL AND METHOD OF MANUFACTURING ULTRASONIC TREATMENT TOOL

(71) Applicant: Olympus Corporation, Tokyo (JP)

(72) Inventor: Seigo Kase, Tokyo (JP)

(73) Assignee: Olympus Corporation, Tokyo (JP)

( * ) Notice: Subject to any disclaimer, the term of this patent is extended or adjusted under 35 U.S.C. 154(b) by 422 days.

(21) Appl. No.: 18/158,787

(22) Filed: Jan. 24, 2023

(65) Prior Publication Data

US 2023/0157717 A1 May 25, 2023

Related U.S. Application Data

(63) Continuation of application No. PCT/JP2020/029857, filed on Aug. 4, 2020.

(51) Int. Cl.
*A61B 17/32* (2006.01)

(52) U.S. Cl.
CPC .......... *A61B 17/320092* (2013.01); *A61B 2017/320095* (2017.08)

(58) Field of Classification Search
CPC .......... A61B 17/320092; A61B 2017/320093; A61B 2017/320094; A61B 2017/320095
See application file for complete search history.

(56) References Cited

U.S. PATENT DOCUMENTS

| | | |
|---|---|---|
| 2013/0303949 A1 | 11/2013 | Kawaguchi et al. |
| 2018/0098809 A1 | 4/2018 | Miyazaki |

FOREIGN PATENT DOCUMENTS

| | | |
|---|---|---|
| JP | 2012531970 A | 12/2012 |
| WO | WO-2011002797 A1 | 1/2011 |
| WO | WO-2013062103 A1 | 5/2013 |
| WO | WO-2016208384 A1 | 12/2016 |

OTHER PUBLICATIONS

"International Application Serial No. PCT/JP2020/029857, International Search Report dated Oct. 6, 2020", (Jun. 10, 2020), 2 pgs.

*Primary Examiner* — Ashley L Fishback
(74) *Attorney, Agent, or Firm* — Schwegman Lundberg & Woessner, P.A.

(57) ABSTRACT

An ultrasonic treatment includes: a vibration transmission portion configured to vibrate by receiving ultrasonic waves, and transmit vibration to a treatment target; a sheath that includes a first through hole in which the vibration transmission portion is inserted while a distal end of the vibration transmission portion is exposed, and a second through hole that has a hole shape penetrating in a different direction from a penetration direction of the first through hole; a jaw that includes a first hole portion in which the sheath is inserted and a second hole portion configured to communicate with the second through hole; and a shaft that includes a space in which the vibration transmission portion is inserted, and that allows the jaw to rotate relative to the sheath when the shaft is inserted in the second through hole and the second hole portion.

12 Claims, 16 Drawing Sheets

ULTRASONIC TREATMENT TOOL AND METHOD OF MANUFACTURING ULTRASONIC TREATMENT TOOL

CROSS-REFERENCE TO RELATED APPLICATION

This application is a continuation of International Application No. PCT/JP2020/029857, filed on Aug. 4, 2020, the entire contents of which are incorporated herein by reference.

BACKGROUND

1. Technical Field

The present disclosure relates to an ultrasonic treatment tool and a method of manufacturing the ultrasonic treatment tool.

2. Related Art

As a medical treatment tool, an ultrasonic treatment tool that performs treatment on living tissue by using ultrasonic vibration is known. For example, an ultrasonic treatment tool that includes a vibration transmission portion for transmitting ultrasonic vibration and a jaw that is arranged in a rotatable manner on the vibration transmission portion is known (for example, Japanese Translation of PCT International Application Publication No. 2012-531970). With use of the ultrasonic treatment tool, an operator, such as a doctor, grips a region (hereinafter, described as a target) as a target for treatment in living tissue by the vibration transmission portion and the jaw that constitute a pair of gripper pieces, applies ultrasonic vibration to the gripped target, and performs cauterization, coagulation, incision, or the like.

SUMMARY

In some embodiments, provided is an ultrasonic treatment tool that is connected to a transducer unit and that receives ultrasonic waves generated and applied by the transducer unit. The ultrasonic treatment tool includes: a vibration transmission portion configured to vibrate by receiving the applied ultrasonic waves, and transmit vibration to a treatment target; a sheath that includes a first through hole in which the vibration transmission portion is inserted while a distal end of the vibration transmission portion is exposed, and a second through hole that has a hole shape penetrating in a different direction from a penetration direction of the first through hole; a jaw that includes a first hole portion in which the sheath is inserted and a second hole portion configured to communicate with the second through hole; and a shaft that includes a space in which the vibration transmission portion is inserted, and that allows the jaw to rotate relative to the sheath when the shaft is inserted in the second through hole and the second hole portion.

In some embodiments, provided is a method of manufacturing an ultrasonic treatment tool that is connected to a transducer unit and that receives ultrasonic waves generated and applied by the transducer unit. The method includes: arranging a jaw on a sheath, the sheath including a first through hole in which a vibration transmission portion is inserted while a distal end of the vibration transmission portion is exposed and a second through hole that has a hole shape penetrating in a different direction from a penetration direction of the first through hole, the vibration transmission portion being configured to vibrate by receiving the applied ultrasonic waves and transmit the vibration to a treatment target, the jaw including a first hole portion in which the sheath is inserted and a second hole portion configured to communicate with the second through hole, the jaw being arranged on the sheath such that the sheath is inserted in the first hole portion and the second through hole communicates with the second hole portion; inserting a shaft, the shaft including a space in which the vibration transmission portion is inserted, into the second through hole and the second hole portion such that the space is aligned with the penetration direction of the first through hole; and inserting the vibration transmission portion into the first through hole and the space of the shaft.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of an ultrasonic treatment tool and a method of manufacturing the ultrasonic treatment tool according to the disclosure will be described below with reference to the drawings. The disclosure is not limited by the embodiments below. Further, in description of the drawings, the same or corresponding components are appropriately denoted by the same reference symbols. Furthermore, it is necessary to note that the drawings are schematic, and dimensional relations among the components, ratios among the components, and the like may be different from the actual ones. Moreover, the drawings may include portions that have different dimensional relations or ratios.

Embodiments

Figure 1:
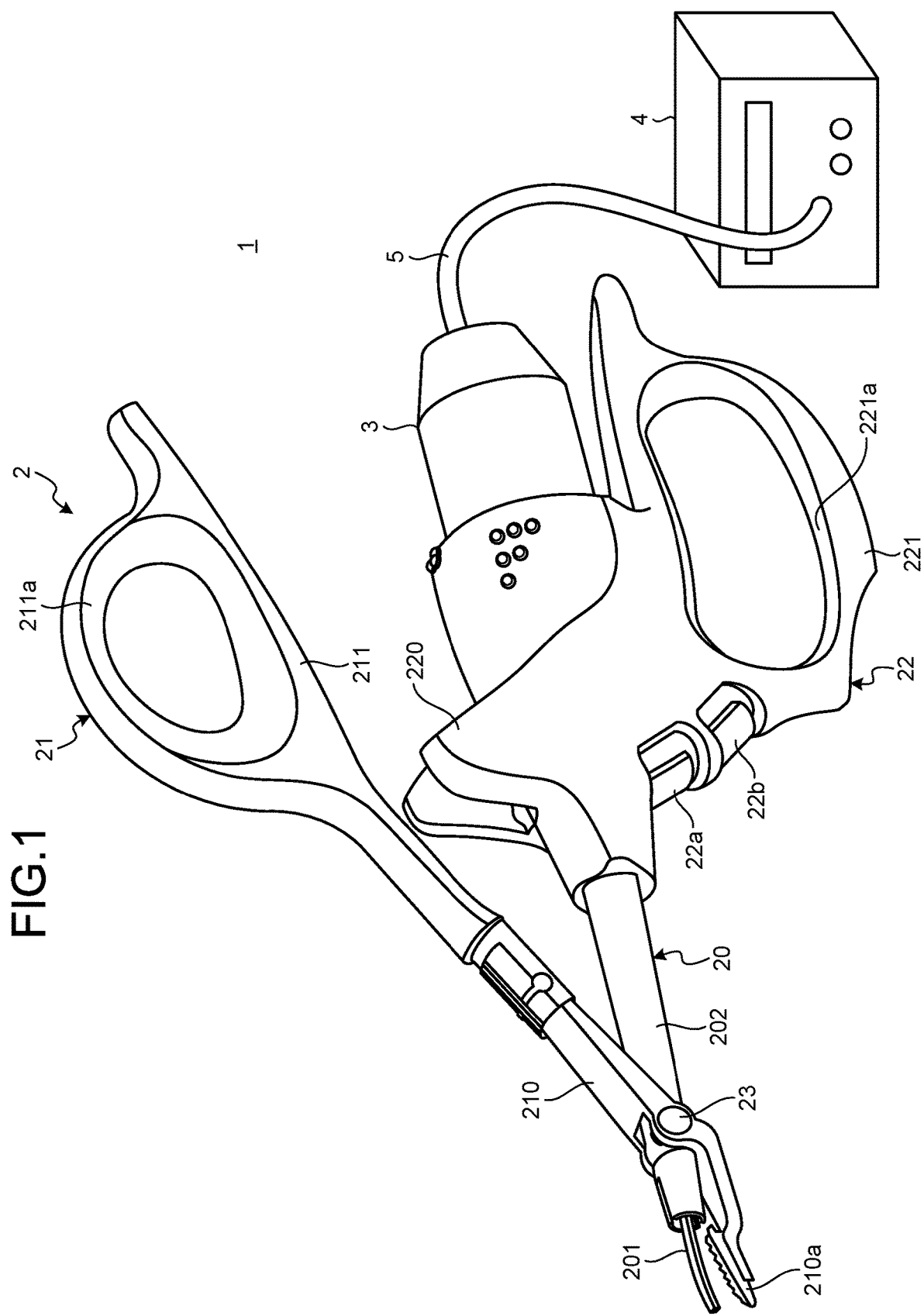
FIG. 1 is a diagram schematically illustrating a treatment system according to one embodiment of the disclosure.

FIG. 1 is a diagram schematically illustrating a treatment system according to one embodiment of the disclosure. A treatment system 1 is a system that grips a region (target) as a target for treatment in living tissue by a pair of gripper pieces and performs cauterization, coagulation, incision, or the like by applying vibration or a high-frequency electric current to the gripped target. The treatment system 1 includes a treatment tool 2, a transducer unit 3, a control device 4, and a connection cable 5.

The treatment tool 2 applies heat to the gripped target and performs cauterization, coagulation, incision, or the like on the target. In this case, the heat applied to the target is frictional heat that is generated by vibration or joule heat that is generated by conduction of a high-frequency electric current. A configuration of the treatment tool 2 will be described later.

The transducer unit 3 generates ultrasonic vibration under the control of the control device 4. The transducer unit 3 includes, for example, an ultrasonic transducer. The ultrasonic transducer includes a piezoelectric element and generates ultrasonic waves by supplying an electric current to the piezoelectric element. The ultrasonic transducer is directly or indirectly connected to the treatment tool 2 (a probe main body 201 to be described later), and transmits the generated ultrasonic waves to the probe main body 201. Further, the transducer unit 3 is electrically connected to the control device 4 via the connection cable 5.

The control device 4 supplies electric power to the transducer unit 3 and the probe main body 201, and controls drive of the transducer unit 3 and supply of a high-frequency electric current to the probe main body 201. The control device 4 is configured with a general-purpose processor, such as a central processing unit (CPU), or a dedicated processor, such as various arithmetic circuits including a field programmable gate array (FPGA) and an application specific integrated circuit (ASIC), for implementing a specific function.

Figure 2:
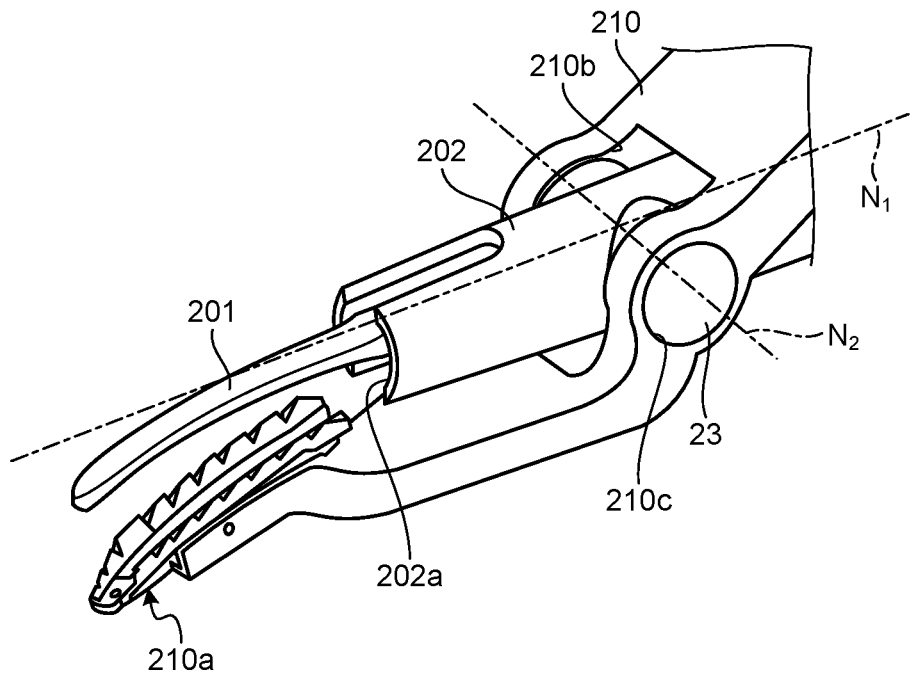
FIG. 2 is a diagram illustrating a distal end structure of a treatment tool illustrated in FIG. 1.
Figure 3:
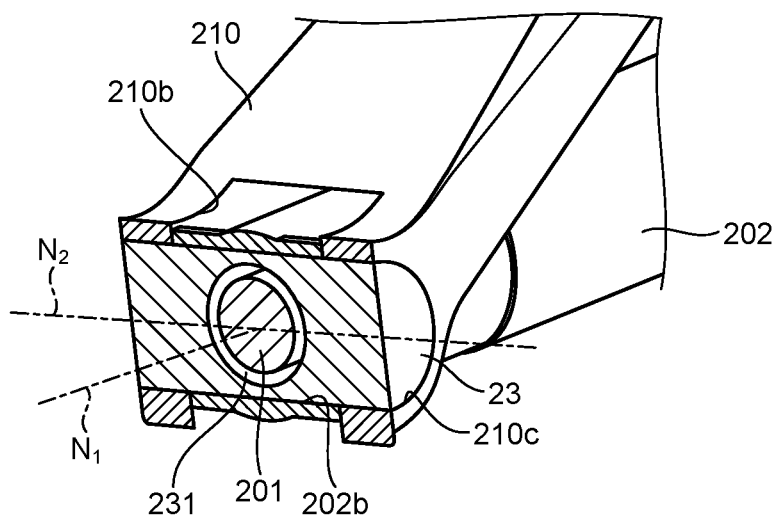
FIG. 3 is a cross-sectional view of the distal end structure illustrated in FIG. 2.
Figure 4:
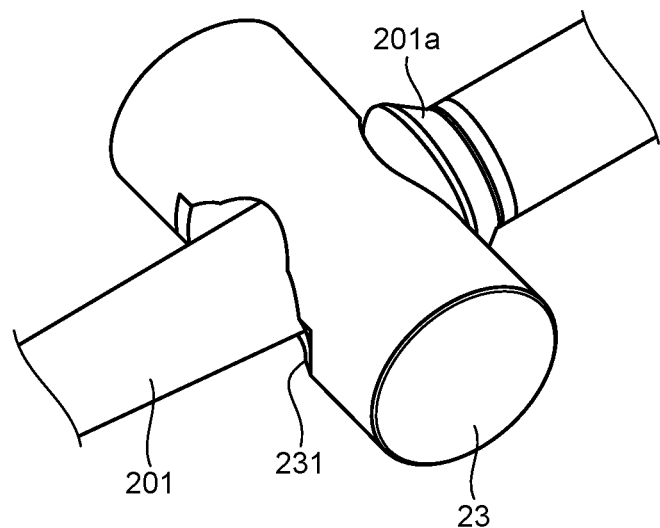
FIG. 4 is a diagram illustrating a configuration of a main part of the distal end structure illustrated in FIG. 2.

The configuration of the treatment tool 2 will be described below. FIG. 2 is a diagram illustrating a distal end structure of the treatment tool illustrated in FIG. 1. FIG. 3 is a cross-sectional view of the distal end structure illustrated in FIG. 2. FIG. 4 is a diagram illustrating a configuration of a main part of the distal end structure illustrated in FIG. 2.

The treatment tool 2 includes a probe portion 20, a first main body portion 21, a second main body portion 22, and a shaft 23.

The probe portion 20 includes the probe main body 201 and a sheath 202.

The first main body portion 21 includes a jaw 210 and a gripped portion 211.

The second main body portion 22 includes a connection portion 220 and a gripped portion 221.

Meanwhile, in the treatment tool 2, a side that is connected to the transducer unit 3 in a longitudinal direction of the sheath 202 will be referred to as a "proximal end" side, and an opposite side will be referred to as a "distal end" side.

The probe main body 201 is configured with a rod. The probe main body 201 is caused to perform longitudinal vibration, which is vibration in a direction parallel to a longitudinal direction of the probe main body 201, by ultrasonic waves transmitted from the transducer unit 3. With heat or friction generated by the longitudinal vibration, the target is subjected to cauterization, coagulation, incision, or the like. Furthermore, high-frequency power is supplied to the probe main body 201 from the control device 4. If the high-frequency power is supplied, a high-frequency electric current flows to the target due to a potential difference between the probe main body 201 and the jaw 210, so that cauterization, coagulation, or the like is performed. The probe main body 201 corresponds to a vibration transmission portion.

The sheath 202 has a tubular shape. The probe main body 201 is inserted in the sheath 202, and the sheath 202 surrounds the probe main body 201.

The jaw 210 is arranged in a rotatable manner on the probe portion 20. The jaw 210 rotates about an axis (a central axis $N_2$ to be described later) that penetrates through the sheath 202 and that is perpendicular to a longitudinal axis $N_1$ of the sheath 202. Further, the jaw 210 grips, at one end thereof, the target in cooperation with the probe main body 201. Specifically, a gripper 210a is arranged on one end of the jaw 210. The jaw 210 holds the gripper 210a in a swingable manner. The gripper 210a rotates about an axis that extends in a direction perpendicular to the longitudinal axis $N_1$ of the sheath 202, for example. Furthermore, another end of the jaw 210 is connected to the gripped portion 211.

The gripped portion 211 is a portion that is to be gripped by an operator. In the gripped portion 211, a through hole 211a that is fitted to a part (for example, a thumb) of a hand of the operator is formed.

The connection portion 220 holds the sheath 202 and is connected to the transducer unit 3.

The gripped portion 221 is a portion that is to be gripped by the operator. In the gripped portion 221, a through hole 221a that is fitted to another part (for example, a forefinger or a middle finger) of the hand of the operator is formed.

Operation buttons 22a and 22b are arranged in the second main body portion 22. For example, the operation button 22a is a button for causing the probe main body 201 to generate ultrasonic vibration. Further, the operation button 22b is a button for supplying high-frequency voltage to the probe main body 201 and causing a high-frequency electric current to flow through the target. Each of the buttons outputs a signal to the control device 4 by being pressed by the operator. The control device 4 drives the transducer unit 3 or supplies high-frequency voltage to the probe main body 201 in accordance with the input signal.

The shaft 23 has a columnar shape and is arranged so as to penetrate through the sheath 202 and the jaw 210. The shaft 23 is held by the sheath 202. Further, the jaw 210 is mounted on both ends of the shaft 23. The jaw 210 is able to slide relative to the shaft 23, and is rotatable relative to the sheath 202. Specifically, the shaft 23 penetrates through the jaw 210 at both end portions, and allows the jaw 210 to freely rotate about the central axis $N_2$. The central axis $N_2$ is a central axis of the shaft 23, crosses the probe main body 201, and is perpendicular to the longitudinal axis $N_1$ of the sheath 202.

Further, a through hole 231 through which the probe main body 201 penetrates is formed in the shaft 23. The through hole 231 forms a space in which the probe main body 201 is inserted.

Here, in the probe main body 201, a lining 201a that comes in contact with the sheath 202, that maintains a positional relationship between the probe main body 201 and the sheath 202, and that reduces friction is arranged (see FIG. 4). In the present embodiment, the lining 201a is arranged at a position that comes in contact with a rear end side of the shaft 23. The lining 201a comes in contact with the shaft 23, and therefore, is able to prevent rotation of the shaft 23 about the central axis $N_2$.

The treatment tool 2 is able to rotate the jaw 210 about the shaft 23 (the central axis $N_2$) relative to the probe main body 201, by operation of the gripped portions 211 and 221. After the jaw 210 is rotated and the probe main body 201 and the gripper 210a grip the target, if the operation buttons 22a and 22b are pressed, energy that is caused by ultrasonic waves or high-frequency power is supplied to the probe main body 201 under the control of the control device 4. By supplying the energy to the probe main body 201, the target is subjected to cauterization, coagulation, incision, or the like.

A method of manufacturing the treatment tool 2 will be described below with reference to FIG. 5 to FIG. 8. FIG. 5 to FIG. 8 are diagrams for explaining the method of manufacturing the treatment tool illustrated in FIG. 1.

Figure 5:
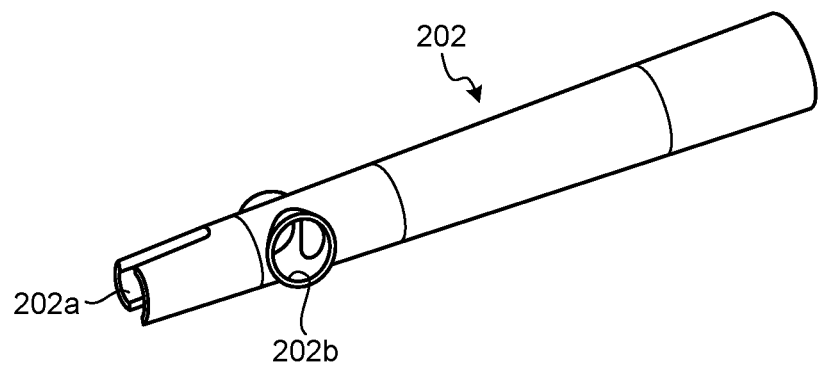
FIG. 5 is a first diagram for explaining a method of manufacturing the treatment tool illustrated in FIG. 1.

First, the sheath 202 is prepared (see FIG. 5). In the sheath 202, a first through hole 202a in which the probe main body 201 is inserted and a second through hole 202b in which the shaft 23 is inserted are formed.

Figure 6:
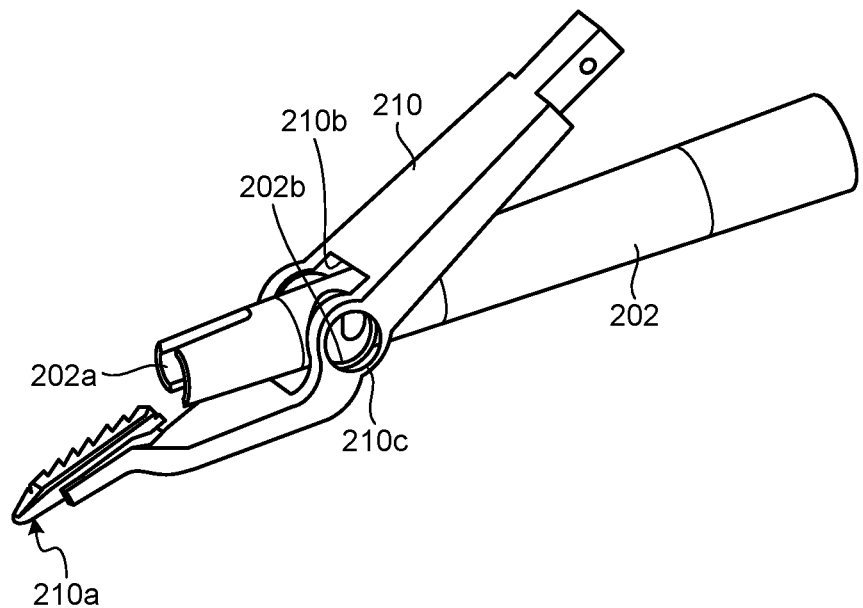
FIG. 6 is a second diagram for explaining the method of manufacturing the treatment tool illustrated in FIG. 1.

The jaw 210 is arranged on the sheath 202 (see FIG. 6). In the jaw 210, a first hole portion 210b in which the sheath 202 is inserted and a second hole portion 210c in which the shaft 23 is inserted are formed. A penetration direction of the first hole portion 210b and a penetration direction of the second hole portion 210c are different from each other, and the holes cross each other. The second hole portion 210c has a hole shape that is extended from mutually-different side portions of the first hole portion 210b. Here, the side portions of the first hole portion 210b correspond to wall portions (thickness portions) that form a hole. The jaw 210 is arranged at a position at which the second hole portion 210c communicates with the second through hole 202b.

Meanwhile, in this case, the gripped portion 211 may be mounted on the jaw 210.

Figure 7:
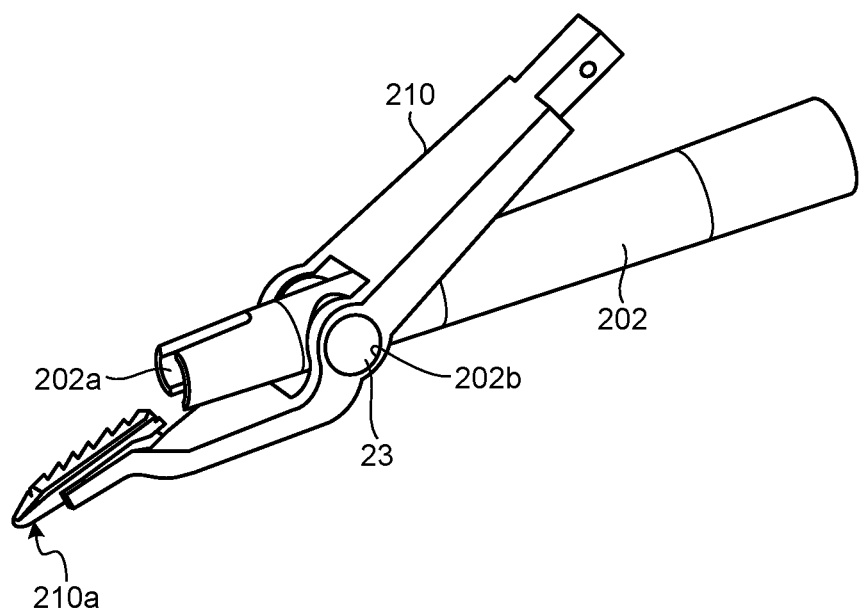
FIG. 7 is a third diagram for explaining the method of manufacturing the treatment tool illustrated in FIG. 1.

Thereafter, the shaft 23 is inserted in the second through hole 202b and the second hole portion 210c (see FIG. 7). The shaft 23 allows the jaw 210 to freely rotate relative to the sheath 202. In this case, the shaft 23 is arranged such that a penetration direction of the through hole 231 and a penetration direction of the sheath 202 are aligned.

Figure 8:
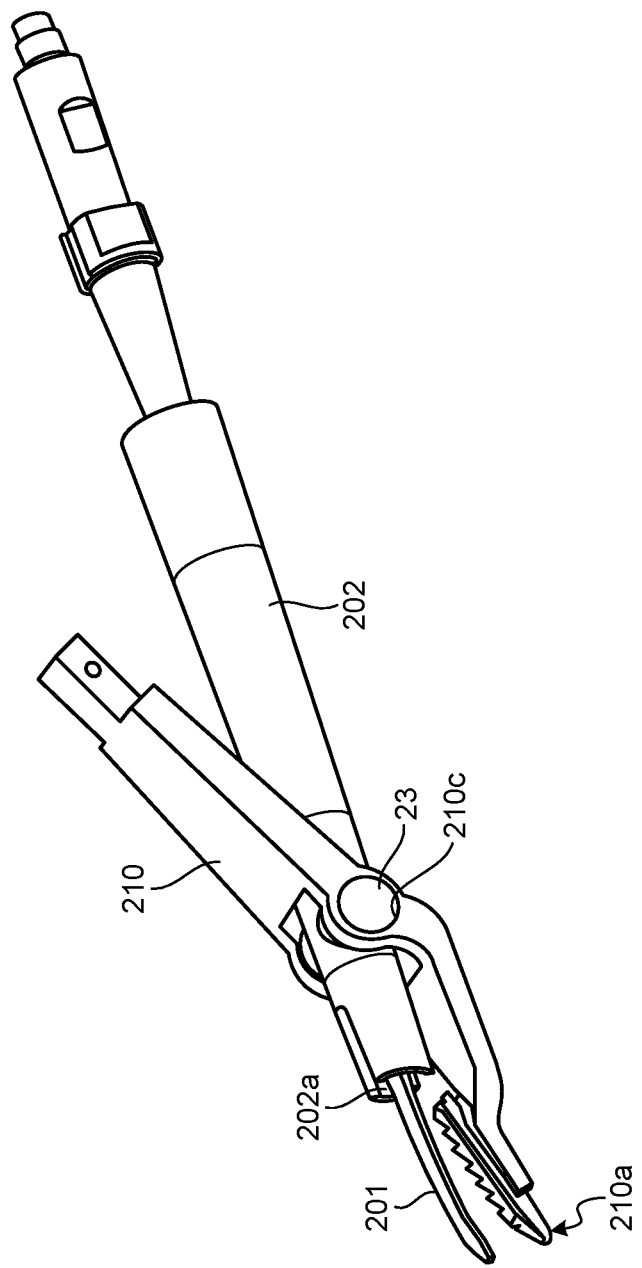
FIG. 8 is a fourth diagram for explaining the method of manufacturing the treatment tool illustrated in FIG. 1.

After the shaft 23 is arranged, the probe main body 201 is inserted in the sheath 202 (see FIG. 8). In this case, the probe main body 201 penetrates through the shaft 23 via the through hole 231. Further, a distal end portion of the probe main body 201 is exposed to outside in a state in which the probe main body 201 is arranged on the sheath 202.

Thereafter, the gripped portion 211 is mounted on the jaw 210, and the second main body portion 22 is mounted on the sheath 202, so that the treatment tool 2 is manufactured.

According to the embodiment of the disclosure as described above, the shaft 23 that penetrates through the sheath 202 and the jaw 210 allows the jaw 210 to rotate about the central axis $N_2$. According to the present embodiment, the probe main body 201, the sheath 202, the jaw 210, and the shaft 23 allow the gripper 210a to freely rotate relative to the probe main body 201 that is the vibration transmission portion, so that it is possible to prevent interference between the vibration transmission portion and the jaw and mount the jaw in a rotatable manner with a simple configuration.

First Modification

Figure 9:
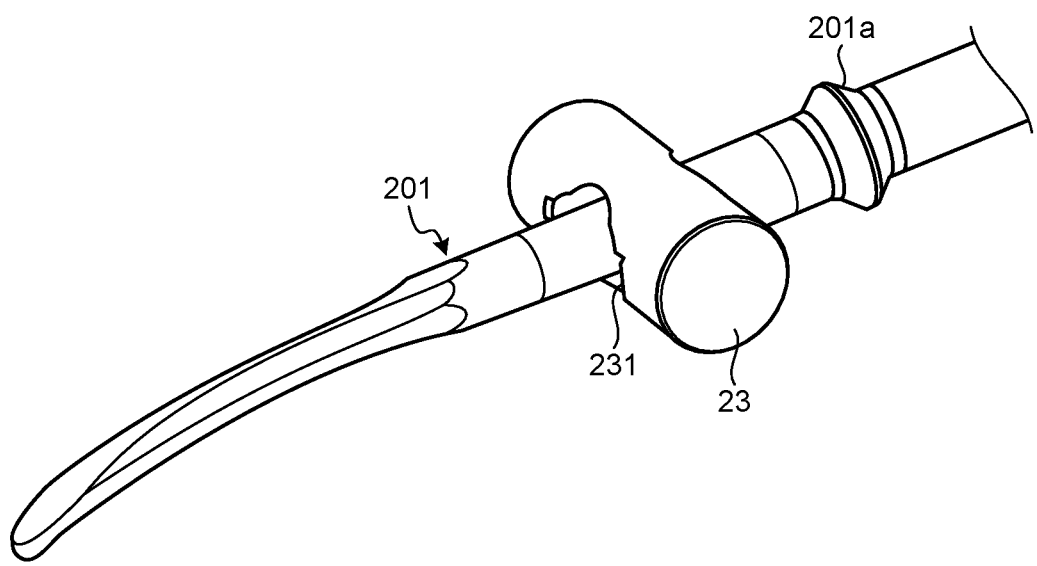
FIG. 9 is a diagram for explaining a configuration of a main part of a treatment tool according to a first modification.

A first modification of the embodiment will be described below with reference to FIG. 9. FIG. 9 is a diagram for explaining a configuration of a main part of a treatment tool according to the first modification. Meanwhile, a configuration of a treatment system according to the first modification is the same as the treatment system 1 as described above except that arrangement of the lining 201a is changed, and therefore, explanation of the components other than the lining 201a will be omitted. A configuration that is different from the embodiment will be described below.

The lining 201a according to the first modification is arranged at a position that is located on a rear end side relative to the shaft 23 and that does not come in contact with the shaft 23.

In the first modification as described above, the position of the lining 201a is changed as compared to the embodiment as described above, but a behavior of the treatment tool itself is not changed, so that it is possible to achieve the same effects as the embodiment.

Second Modification

Figure 10:
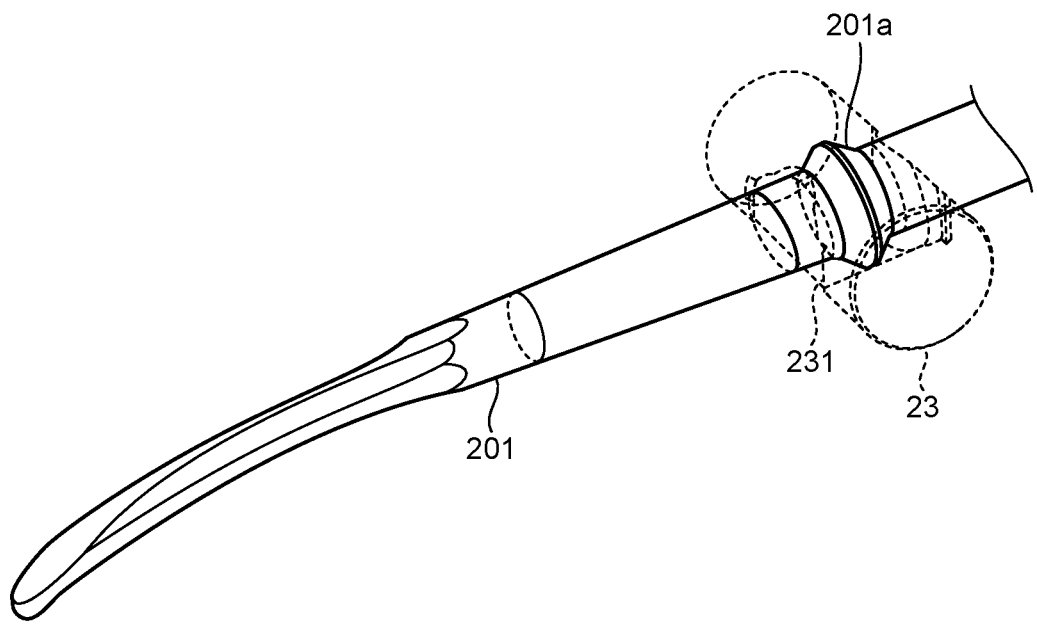
FIG. 10 is a diagram for explaining a configuration of a main part of a treatment tool according to a second modification.

A second modification of the embodiment will be described below with reference to FIG. 10. FIG. 10 is a diagram for explaining a configuration of a main part of a treatment tool according to the second modification. Meanwhile, a configuration of a treatment system according to the second modification is the same as the treatment system 1 as described above except that arrangement of the lining 201a is changed. A configuration that is different from the embodiment will be described below.

The lining 201a according to the second modification is arranged inside the shaft 23. The lining 201a comes in contact with an inner peripheral surface of the through hole 231 of the shaft 23, and determines a position of the probe main body 201 relative to the sheath 202 and the shaft 23.

In the second modification as described above, the position of the lining 201a is changed as compared to the embodiment as described above, but a behavior of the treatment tool itself is not changed, so that it is possible to achieve the same effects as the embodiment.

Third Modification

Figure 11:
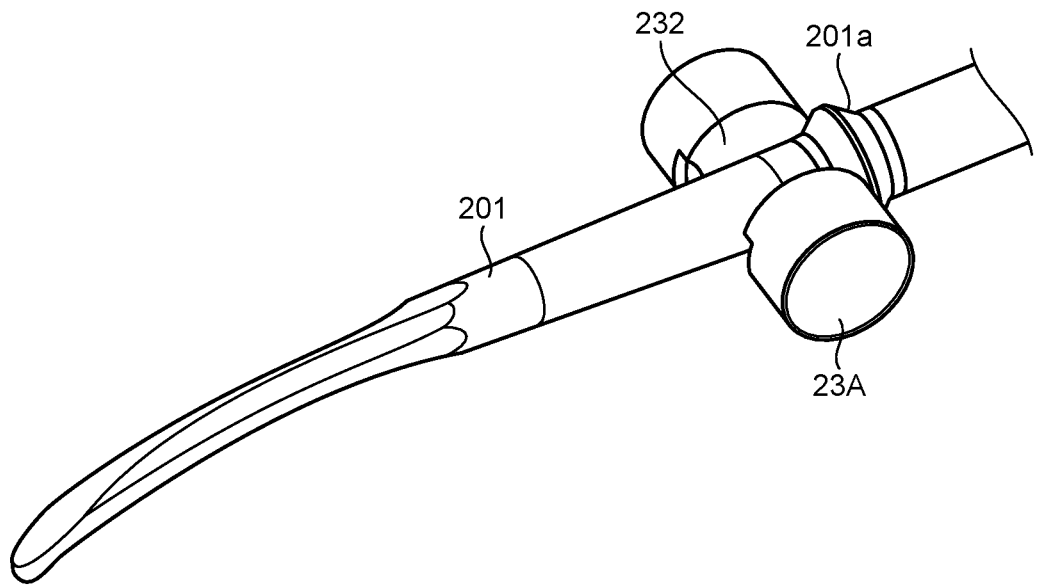
FIG. 11 is a first diagram for explaining a configuration of a main part of a treatment tool according to a third modification.
Figure 12:
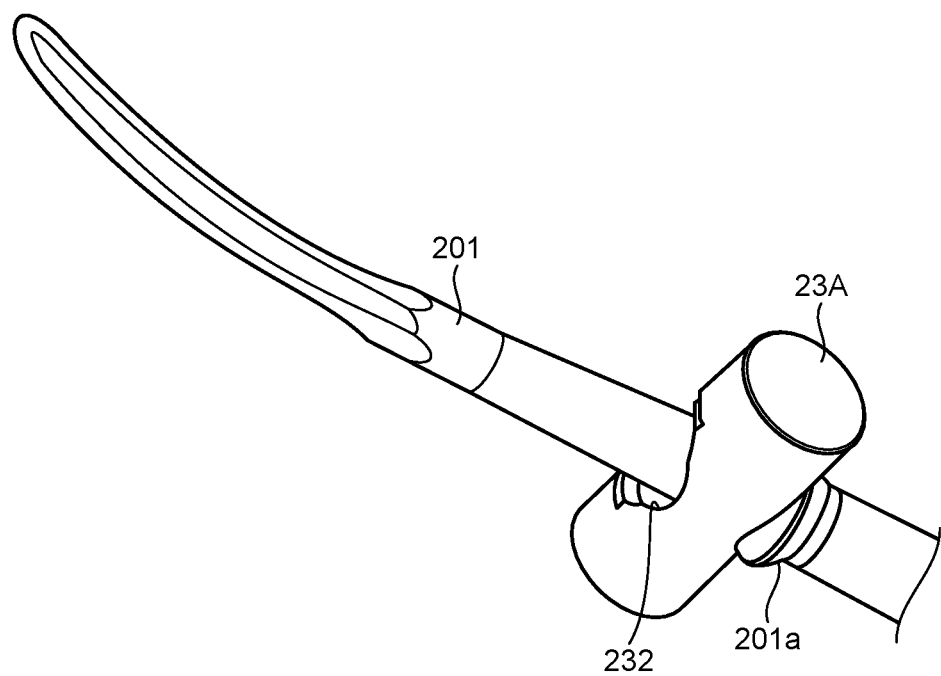
FIG. 12 is a second diagram for explaining the configuration of the main part of the treatment tool according to the third modification.

A third modification of the embodiment will be described below with reference to FIG. 11 and FIG. 12. FIG. 11 and FIG. 12 are diagrams for explaining a configuration of a main part of a treatment tool according to the third modification. Meanwhile, a configuration of a treatment system according to the third modification is the same as the treatment system 1 as described above except that the shaft 23 is replaced with a shaft 23A. A configuration that is different from the embodiment will be described below.

The shaft 23A has a columnar shape. In the shaft 23A, a notch portion 232 is formed by cutting a central portion. The notch portion 232 forms a space in which the probe main body 201 is inserted. The notch portion 232 is formed by cutting the central portion of the shaft 23A in a partially connected manner.

In the third modification as described above, the configuration of the shaft 23A is changed as compared to the embodiment as described above, but a behavior of the treatment tool itself is not changed, so that it is possible to achieve the same effects as the embodiment.

Fourth Modification

Figure 13:
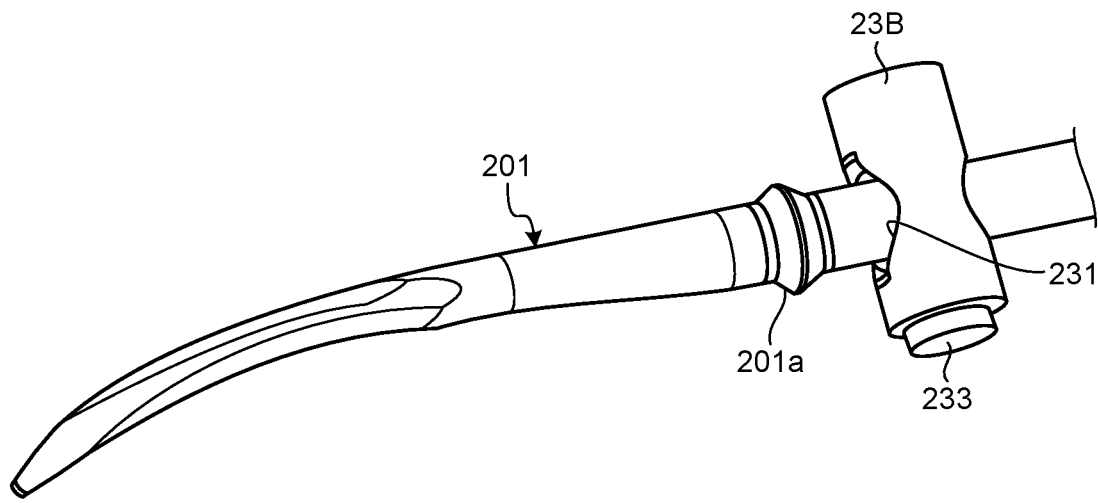
FIG. 13 is a diagram for explaining a configuration of a main part of a treatment tool according to a fourth modification.

A fourth modification of the embodiment will be described below with reference to FIG. 13. FIG. 13 is a diagram for explaining a configuration of a main part of a treatment tool according to the fourth modification. Meanwhile, a configuration of a treatment system according to the fourth modification is the same as the treatment system 1 as described above except that the shaft 23 is replaced with a shaft 23B and a position of the lining 201a is changed. A configuration that is different from the embodiment will be described below.

The shaft 23B has a columnar shape. In the shaft 23B, the through hole 231 through which the probe main body 201 penetrates is formed. Further, one end portion of the shaft 23B has a protruding shape. Specifically, the shaft 23B includes a protruding portion 233 that is arranged on one end portion and has a columnar shape with a smaller diameter than other portions. The protruding portion 233 is inserted in the jaw 210 (the second hole portion 210c on one end side in the direction of the central axis $N_2$) at the time of assembly of the treatment tool, and holds the jaw 210 in a rotatable manner. Meanwhile, in the fourth modification, the second hole portion 210c has a certain shape that conforms to a connection portion of the shaft 23B.

Further, the lining 201a according to the fourth modification is arranged on a distal end side relative to the shaft 23B. The lining 201a comes in contact with the inner peripheral surface of the sheath 202 on the distal end side relative to the shaft 23B, and determines a position of the probe main body 201 relative to the sheath 202.

In the fourth modification as described above, the configuration of the shaft 23B and the position of the lining 201a are changed as compared to the embodiment as described above, but a behavior of the treatment tool itself is not changed, so that it is possible to achieve the same effects as the embodiment.

Meanwhile, the arrangement of the lining 201a according to the fourth modification may be adopted to the embodiment and the second modification.

Fifth Modification

Figure 14:
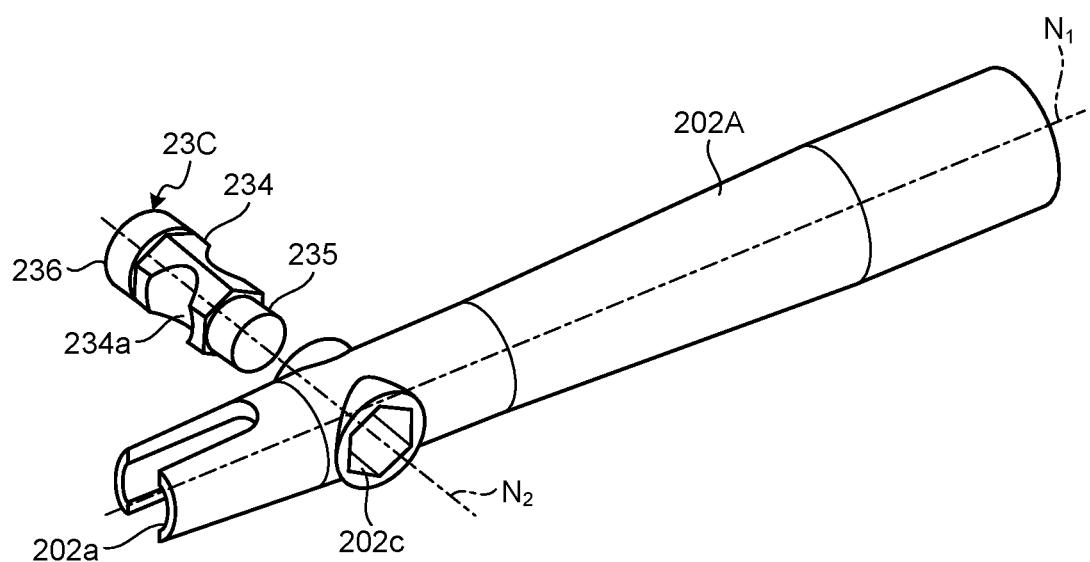
FIG. 14 is an exploded perspective view for explaining a configuration of a main part of a treatment tool according to a fifth modification.
Figure 15:
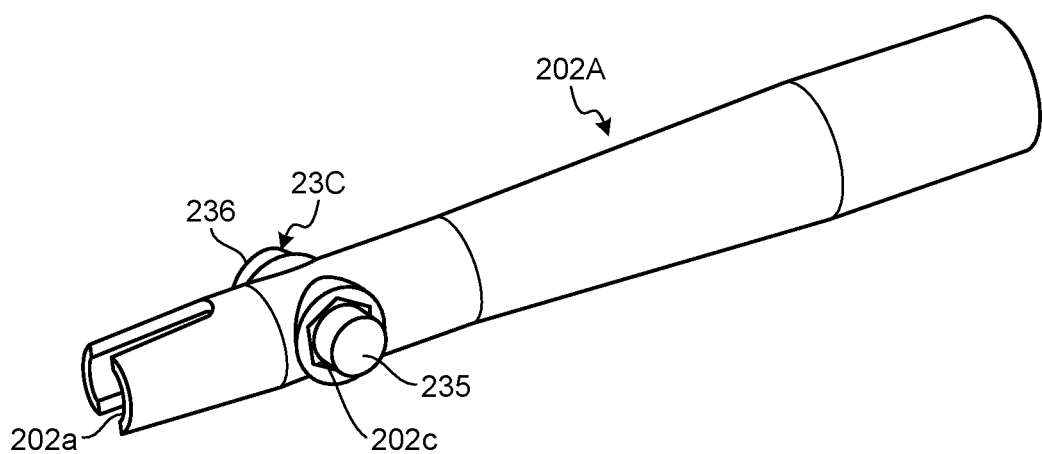
FIG. 15 is a first diagram for explaining the configuration of the main part of the treatment tool according to the fifth modification.
Figure 16:
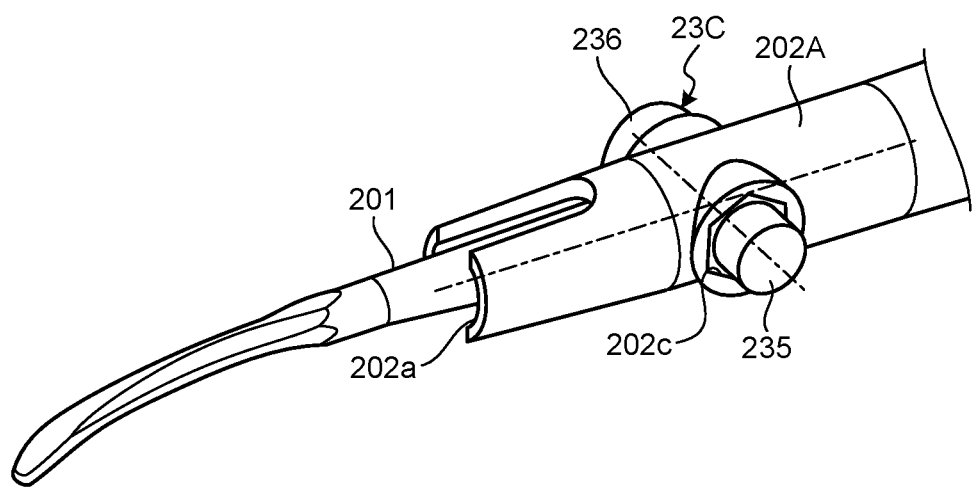
FIG. 16 is a second diagram for explaining a configuration of the main part of the treatment tool according to the fifth modification.

A fifth modification of the embodiment will be described below with reference to FIG. 14 to FIG. 16. FIG. 14 is an exploded perspective view for explaining a configuration of a main part of a treatment tool according to the fifth modification. FIG. 15 and FIG. 16 are diagrams for explaining a configuration of a main part of a treatment tool according to the fifth modification. Meanwhile, a configuration of a treatment system according to the fifth modification is the same as the treatment system 1 as described above except that the shaft 23 is replaced with a shaft 23C and the sheath 202 is replaced with a sheath 202A. A configuration that is different from the embodiment will be described below.

The shaft 23C has a pillar shape. The shaft 23C includes a main body 234 through which the probe main body 201 penetrates, a first end portion 235 that is arranged on one end of the main body 234 and holds the jaw 210, and a second end portion 236 that is arranged on the other end of the main body 234 and holds the jaw 210. In the main body 234, a through hole 234a through which the probe main body 201 penetrates is formed. Further, the main body 234 has a prism shape and extends in the direction of the central axis $N_2$. Meanwhile, in the fifth modification, the second hole portion 210c has a certain shape that conforms to the first end portion 235 and the second end portion 236 of the shaft 23C.

The sheath 202A has a cylindrical shape. In the sheath 202A, the first through hole 202a in which the probe main body 201 is inserted and a second through hole 202c in which the shaft 23C is inserted are formed. In the second through hole 202c, an inner wall surface having a prism shape that conforms to an outer shape of the main body 234 is formed.

When the shaft 23C is inserted in the sheath 202A, the main body 234 and the second through hole 202c are fitted to each other (see FIG. 15). With this fitting, rotation of the shaft 23C about the central axis $N_2$ is prevented.

After arranging the shaft 23C, the probe main body 201 is inserted in the sheath 202 (see FIG. 16). In this case, the probe main body 201 penetrates through the shaft 23C via the through hole 234a.

Thereafter, the gripped portion 211 is mounted on the jaw 210, and the second main body portion 22 is mounted on the sheath 202A, so that the treatment tool is manufactured.

In the fifth modification as described above, the configurations of the shaft 23C and the sheath 202A are changed as compared to the embodiment as described above, but a behavior of the treatment tool itself is not changed, so that it is possible to achieve the same effects as the embodiment.

In addition, in the fifth modification, the shaft 23C and the sheath 202A are fitted to each other and rotation of the shaft 23C relative to the sheath 202A is prevented, so that it is possible to prevent positional deviation of the through hole 234a at the time of assembly.

Sixth Modification

Figure 17:
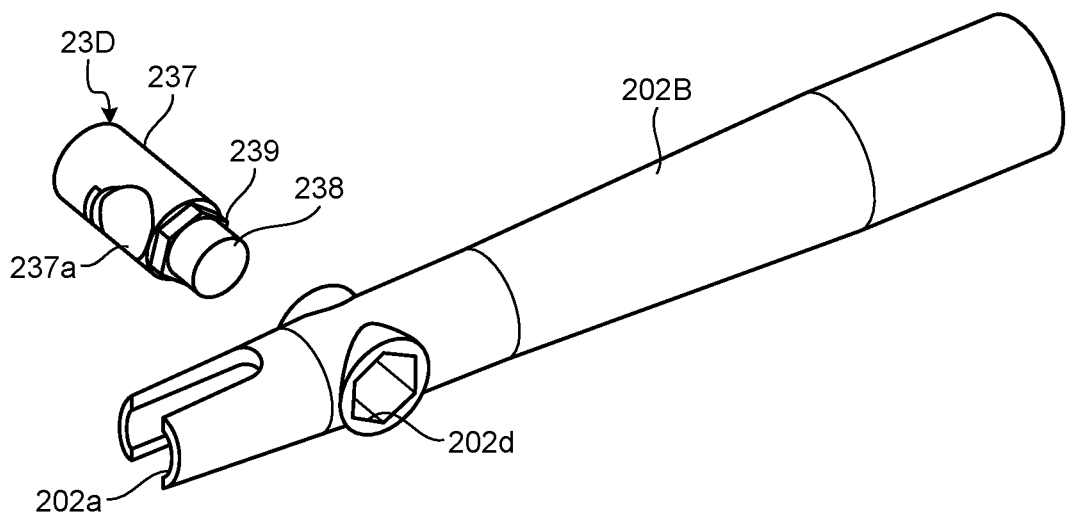
FIG. 17 is an exploded perspective view for explaining a configuration of a main part of a treatment tool according to a sixth modification.

A sixth modification of the embodiment will be described below with reference to FIG. 17. FIG. 17 is an exploded perspective view for explaining a configuration of a main part of a treatment tool according to the fifth modification. Meanwhile, a configuration of a treatment system according to the sixth modification is the same as the treatment system 1 as described above except that the shaft 23 is replaced with a shaft 23D and the sheath 202 is replaced with a sheath 202B. A configuration that is different from the embodiment will be described below.

The shaft 23D has a pillar shape. The shaft 23D includes a main body 237 through which the probe main body 201 penetrates and which holds the jaw 210 at one end side of the main body 237, an end portion 238 that is arranged on the other end side of the main body 237 and that holds the jaw 210, and a prism portion 239 that is arranged between the main body 237 and the end portion 238 and that has a prism shape. In the main body 237, a through hole 237a through which the probe main body 201 penetrates is formed. Meanwhile, in the sixth modification, the second hole portion 210c has a certain shape that conforms to the main body 237 and the end portion 238 of the shaft 23C.

The sheath 202B has a cylindrical shape. In the sheath 202B, the first through hole 202a in which the probe main body 201 is inserted and a second through hole 202d in which the shaft 23D is inserted are formed. In the second through hole 202d, an inner wall surface having a prism shape that conforms to an outer shape of the prism portion 239 is formed on one end side.

At the time of assembly of the treatment tool, when the shaft 23D is inserted in the sheath 202B, the prism portion 239 and the second through hole 202d are fitted to each other. With this fitting, rotation of the shaft 23D about the central axis $N_2$ is prevented.

In the sixth modification as described above, the configurations of the shaft 23D and the sheath 202B are changed as compared to the embodiment as described above, but a behavior of the treatment tool itself is not changed, so that it is possible to achieve the same effects as the embodiment.

In addition, in the sixth embodiment, the shaft 23D and the sheath 202B are fitted to each other and rotation of the shaft 23D relative to the sheath 202B is prevented, so that it is possible to prevent positional deviation of the through hole 237a at the time of assembly.

Seventh Modification

Figure 18:
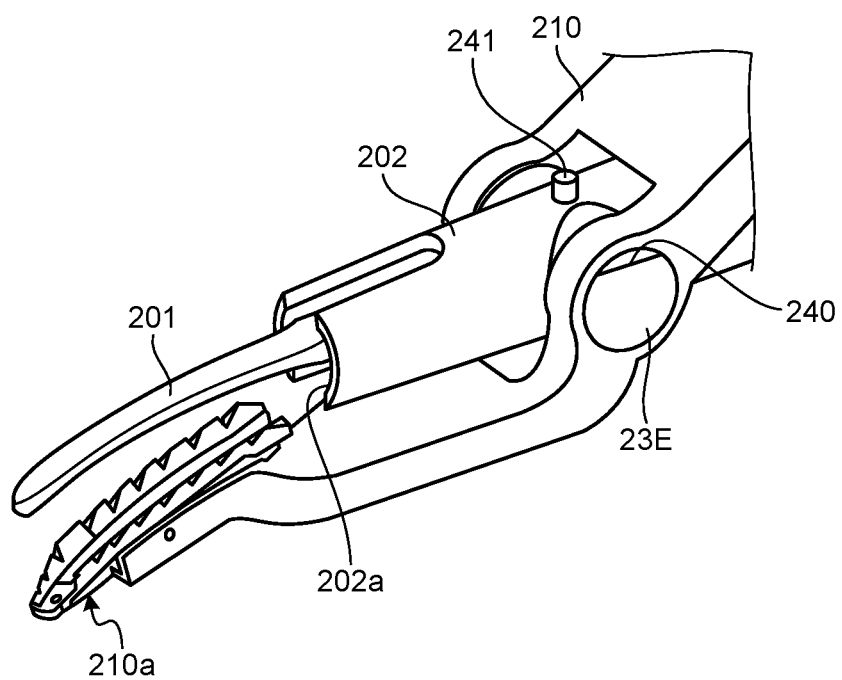
FIG. 18 is a first diagram for explaining a configuration of a main part of a treatment tool according to a seventh modification.
Figure 19:
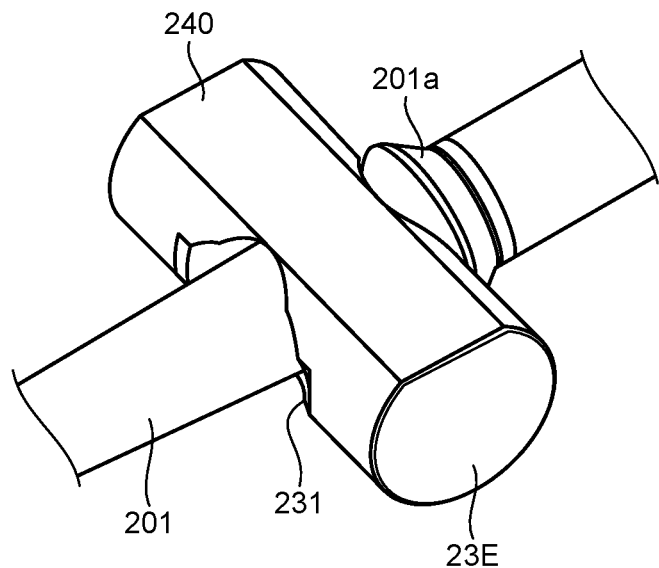
FIG. 19 is a second diagram for explaining the configuration of the main part of the treatment tool according to the seventh modification.

A seventh modification of the embodiment will be described below with reference to FIG. 18 and FIG. 19. FIG. 18 and FIG. 19 are diagrams for explaining a configuration of a main part of a treatment tool according to the third modification. Meanwhile, a configuration of a treatment system according to the seventh modification is the same as the treatment system 1 as described above except that the shaft 23 is replaced with a shaft 23E. A configuration that is different from the embodiment will be described below.

The shaft 23E has a pillar shape. In the shaft 23E, a planar portion 240 is formed by cutting a part of a side surface of the cylinder. The planar portion 240 comes in contact with a pin 241 that penetrates through a part of the sheath 202, in a state in which the shaft 23E is arranged on the sheath 202. The planar portion 240 comes in contact with the pin 241 in the sheath 202, so that rotation of the shaft 23E about the central axis is prevented.

In the seventh modification as described above, the configuration of the shaft 23E is changed as compared to the embodiment as described above, but a behavior of the treatment tool itself is not changed, so that it is possible to achieve the same effects as the embodiment.

In addition, in the seventh modification, the shaft 23E comes in contact with the pin 241, and rotation of the shaft 23E relative to the sheath 202 is prevented, so that it is possible to prevent positional deviation of the through hole 231 at the time of assembly.

Meanwhile, in the seventh modification, it may be possible to prevent rotation of the shaft 23E by forming the second through hole 202b into a certain hole shape that conforms to an outer shape of the shaft 23E, instead of using the pin 241.

Eighth Modification

Figure 20:
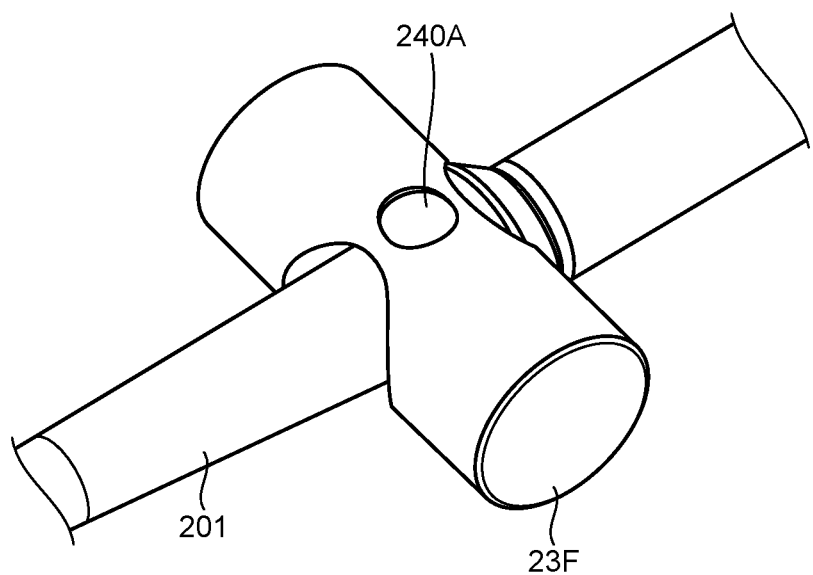
FIG. 20 is a diagram for explaining a configuration of a main part of a treatment tool according to an eighth modification.

An eighth modification of the embodiment will be described below with reference to FIG. 20. FIG. 20 is a diagram for explaining a configuration of a main part of a treatment tool according to the eighth modification. Meanwhile, in the eighth modification, a shaft 23F is provided instead of the shaft 23E of the seventh modification.

The shaft 23F has a pillar shape. A concave portion 240A that comes in contact with the pin 241 is formed on a side surface of the shaft 23F.

In the eighth modification as described above, the configuration of the shaft 23F is changed as compared to the embodiment as described above, but a behavior of the treatment tool itself is not changed, so that it is possible to achieve the same effects as the embodiment.

Furthermore, in the eighth modification, the concave portion 240A of the shaft 23F comes in contact with the pin 241 and rotation of the shaft 23F relative to the sheath 202 is prevented, so that it is possible to prevent positional deviation of the through hole 231 at the time of assembly. Moreover, in the eighth modification, the planar portion (the concave portion 240A) is formed in only the contact portion of the pin 241, so that it is possible to further ensure sliding performance with respect to the jaw 210 and water-tightness with respect to the sheath 202 as compared to the planar portion 240 of the seventh modification.

Ninth Modification

Figure 21:
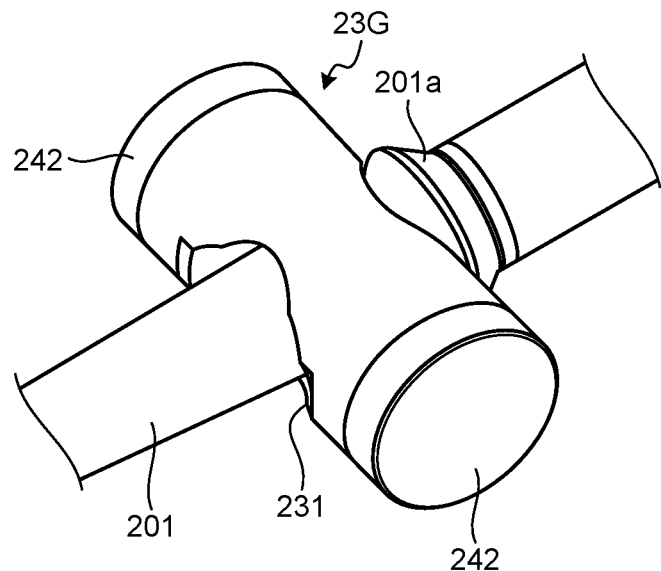
FIG. 21 is a diagram for explaining a configuration of a main part of a treatment tool according to a ninth modification.

A ninth modification of the embodiment will be described below with reference to FIG. 21. FIG. 21 is a diagram for explaining a configuration of a main part of a treatment tool according to the ninth modification. Meanwhile, a configuration of a treatment system according to the ninth modification is the same as the treatment system 1 as described above except that the shaft 23 is replaced with a shaft 23G, and therefore, explanation thereof will be omitted. A configuration that is different from the embodiment will be described below.

The shaft 23G has a pillar shape. Bearings 242 are arranged on both end portions of the shaft 23G. When the shaft 23G is assembled onto the treatment tool, the bearings 242 are held by the jaw 210. Therefore, the jaw 210 is able to smoothly rotate with the aid of the bearings 242. Meanwhile, as long as rotation centers of the bearings match each other and it is possible to mount the jaw in a rotatable manner, the bearings arranged at both ends may have different sizes.

In the ninth modification as described above, the configuration of the shaft 23G is changed as compared to the embodiment as described above, but a behavior of the treatment tool itself is not changed, so that it is possible to achieve the same effects as the embodiment.

In the ninth modification, the bearings 242 restrict rotation of a portion other than the bearings 242 of the shaft 23G caused by rotation of the jaw 210. With this configuration, it is possible to prevent friction between the shaft 23G and the sheath 202, so that it is possible to improve durability of the treatment tool.

Tenth Modification

Figure 22:
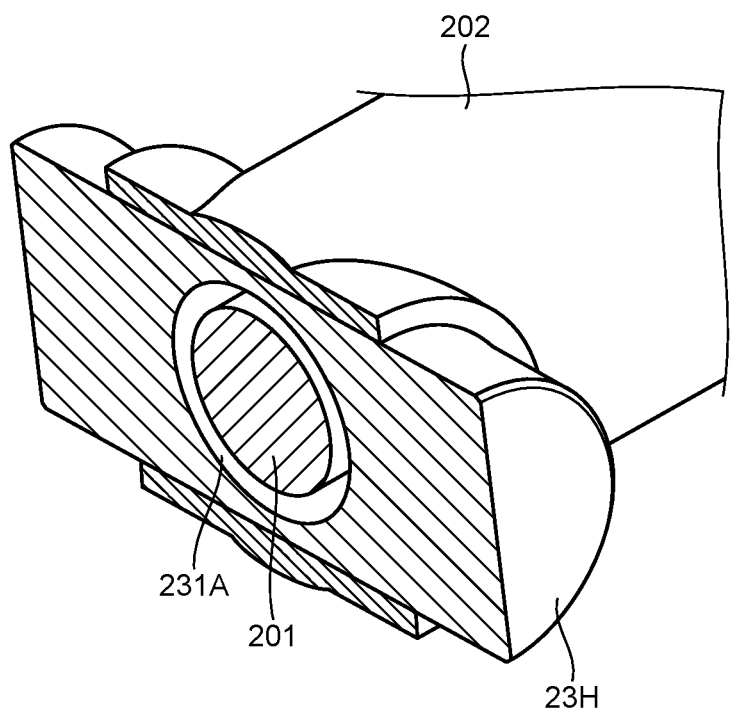
FIG. 22 is a cross-sectional view for explaining a configuration of a main part of a treatment tool according to a tenth modification.
Figure 23:
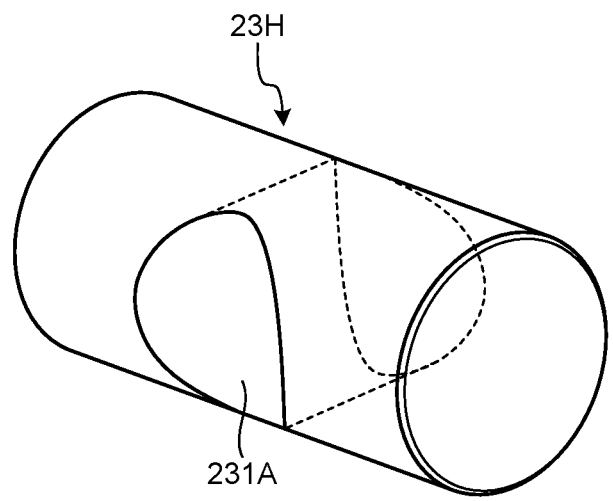
FIG. 23 is a perspective view for explaining the configuration of the main part of the treatment tool according to the tenth modification.

A tenth modification of the embodiment will be described below with reference to FIG. 22 and FIG. 23. FIG. 22 is a cross-sectional view for explaining a configuration of a main part of a treatment tool according to the tenth modification. FIG. 23 is a perspective view for explaining the configuration of the main part of the treatment tool according to the tenth modification. Meanwhile, a configuration of a treatment system according to the tenth modification is the same as the treatment system 1 as described above except that the shaft 23 is replaced with a shaft 23H. A configuration that is different from the embodiment will be described below.

The shaft 23H has a pillar shape. A through hole 231A through which the probe main body 201 penetrates is formed. The through hole 231A forms a space in which the probe main body 201 is inserted. An insulating film is formed on an inner wall surface that is formed by the through hole 231A. Therefore, the probe main body 201 is insulated from the sheath 202 and the jaw 210. Meanwhile, as long as a surface of the inner wall surface of the through hole 231A has insulation property, it is not always needed to provide the insulating film. For example, it may be possible to mount an insulating tubular member on the shaft 23H, and a hole of the tubular member may be adopted as the through hole 231A.

In the tenth modification as described above, the configuration of the shaft 23H is changed as compared to the embodiment as described above, but a behavior of the treatment tool itself is not changed, so that it is possible to achieve the same effects as the embodiment.

In the tenth modification, the probe main body 201 is insulated from the sheath 202 and the jaw 210, and therefore, it is possible to perform treatment while reliably insulating the probe main body 201, which serves as one of poles, and the jaw 210 (and the sheath 202), which serves as the other one of the poles, when a high-frequency electric current flows.

Eleventh Modification

Figure 24:
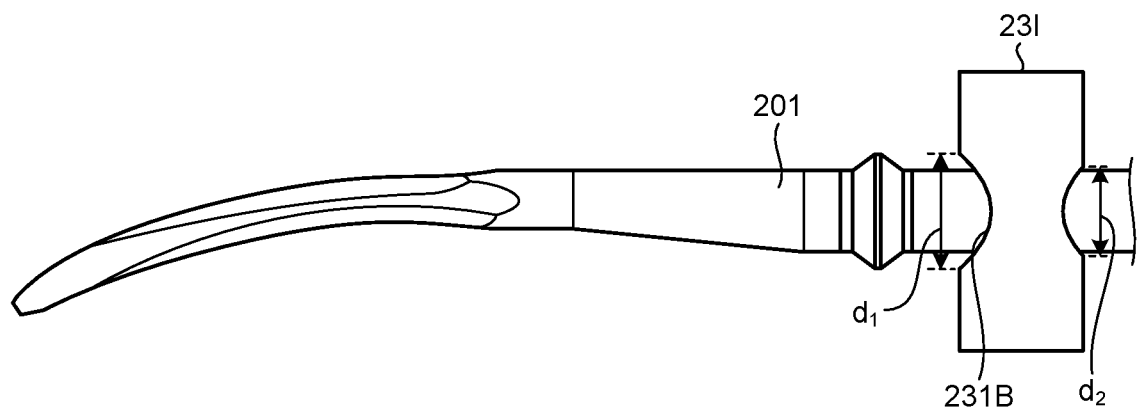
FIG. 24 is a diagram for explaining a configuration of a main part of a treatment tool according to an eleventh modification.

An eleventh modification of the embodiment will be described below with reference to FIG. 24. FIG. 24 is a diagram for explaining a configuration of a main part of a treatment tool according to the eleventh modification. Meanwhile, a configuration of a treatment system according to the eleventh modification is the same as the treatment system 1 as described above except that the shaft 23 is replaced with a shaft 23I. A configuration that is different from the embodiment will be described below.

The shaft 23I has a pillar shape. A through hole 231B through which the probe main body 201 penetrates is formed. The through hole 231B forms a space in which the probe main body 201 is inserted. In the through hole 231B, openings at both ends have different diameters. Specifically, a diameter $d_1$ of the opening located on the distal end side of the probe main body 201 is larger than a diameter $d_2$ of the opening located on the proximal end side of the probe main body 201. Meanwhile, an inner peripheral surface communicating with the both ends may have a shape in which a diameter is changed in a stepped manner or may have a conical shape.

Here, when the probe main body 201 bends while gripping the target, the distal end side bends largely as compared to the proximal end side in the probe main body 201. In the through hole 231B, by increasing the diameter $d_1$ of the opening on the distal end side of the probe main body 201 as compared to the diameter $d_2$ of the opening on the proximal end side, it is possible to cope with a deflection difference of the probe main body 201.

In the eleventh modification as described above, the configuration of the shaft 23I is changed as compared to the embodiment as described above, but a behavior of the treatment tool itself is not changed, so that it is possible to achieve the same effects as the embodiment.

In addition, in the eleventh embodiment, in the through hole 231B, the diameter $d_1$ of the opening on the distal end side of the probe main body 201 is larger than the diameter $d_2$ of the opening on the proximal end side, so that it is possible to prevent interference between the shaft 23I and the probe main body 201 caused by a deflection difference.

Twelfth Modification

Figure 25:
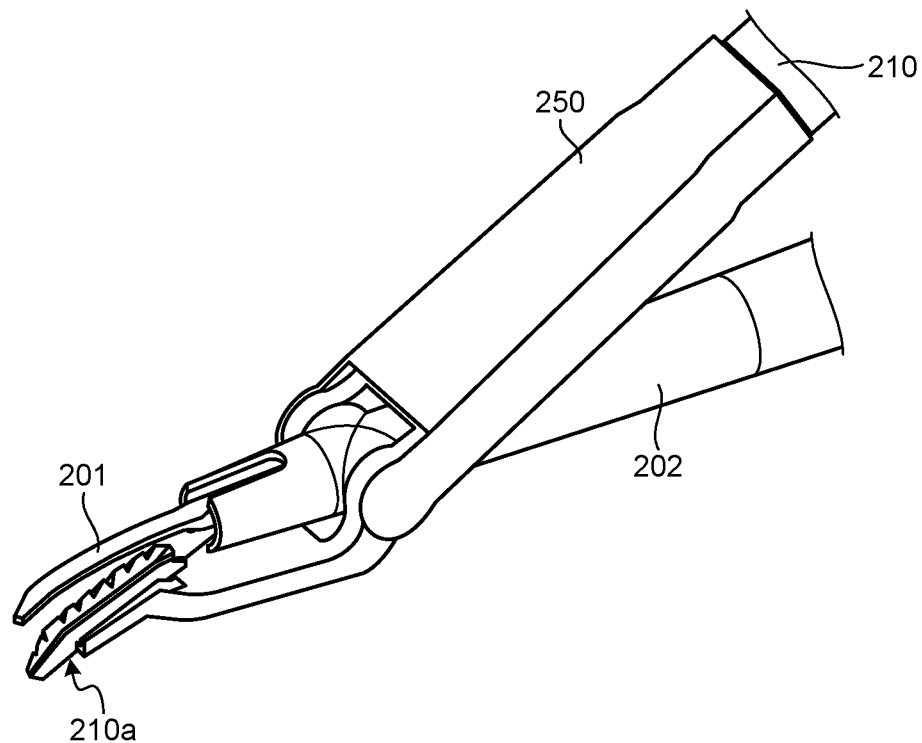
FIG. 25 is a diagram for explaining a configuration of a main part of a treatment tool according to a twelfth modification.
Figure 26:
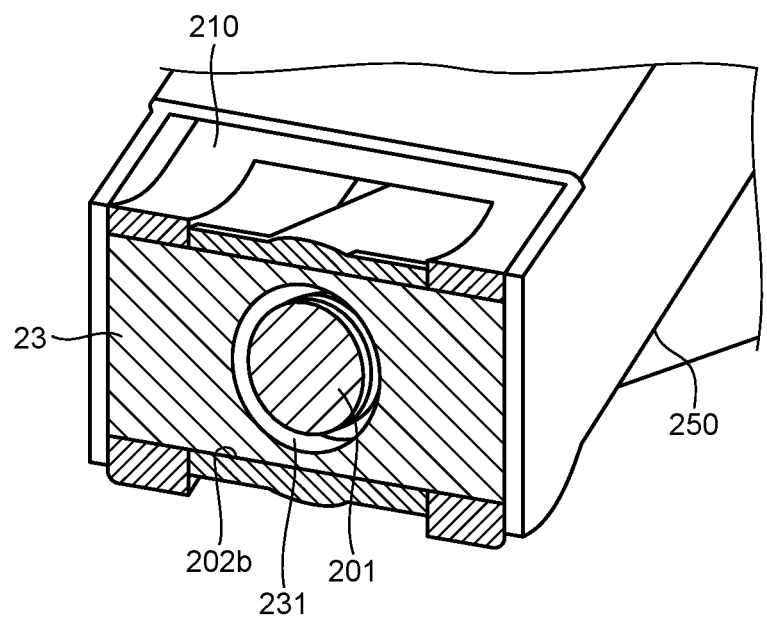
FIG. 26 is a cross-sectional view for explaining the configuration of the main part of the treatment tool according to the twelfth modification.

A twelfth modification of the embodiment will be described below with reference to FIG. 25 and FIG. 26. FIG. 25 is a diagram for explaining a configuration of a main part of a treatment tool according to the twelfth modification. FIG. 26 is a cross-sectional view for explaining the configuration of the main part of the treatment tool according to the twelfth modification. Meanwhile, a configuration of a treatment system according to the twelfth modification is the same as the treatment system 1 as described above except that a cover 250 that covers a part of the jaw 210 is further provided, and therefore, explanation of the configuration other than the cover 250 will be omitted. A configuration that is different from the embodiment will be described below.

The cover 250 extends from an end portion at the side of the gripped portion 211 to a position at which the second hole portion 210c is covered, and covers a part of the jaw 210. Further, the cover 250 covers the both ends of the shaft 23 (see FIG. 26).

In the twelfth modification as described above, the configuration is changed so as to further include the cover 250 in the embodiment as described above, but a behavior of the treatment tool itself is not changed, so that it is possible to achieve the same effects as the embodiment.

Further, in the twelfth modification, the cover 250 that is mounted on the jaw 210 and that covers a part of the jaw 210 covers the both ends of the shaft 23, so that it is possible to prevent coming off of the shaft 23.

Thirteenth Modification

Figure 27:
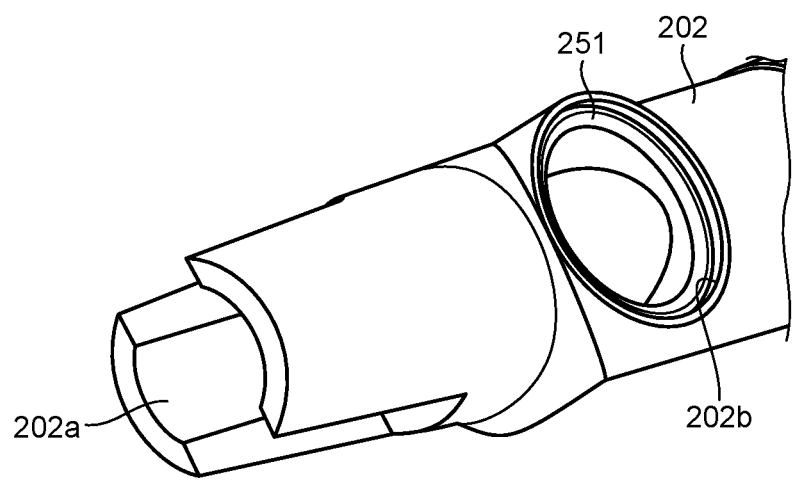
FIG. 27 is a first diagram for explaining a configuration of a main part of a treatment tool according to a thirteenth modification.
Figure 28:
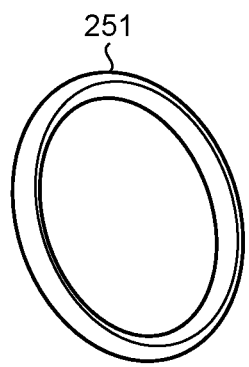
FIG. 28 is a second diagram for explaining the configuration of the main part of the treatment tool according to the thirteenth modification.
Figure 29:
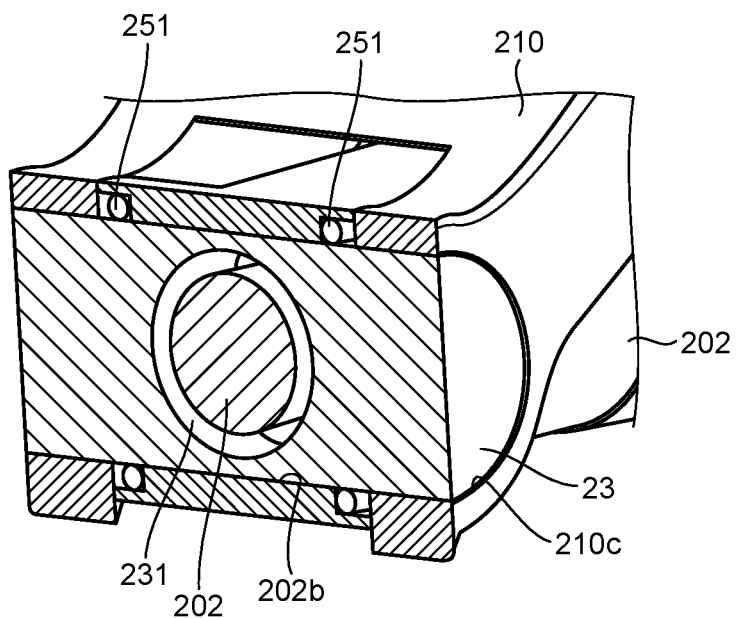
FIG. 29 is a cross-sectional view for explaining the configuration of the main part of the treatment tool according to the thirteenth modification.
Figure 30:
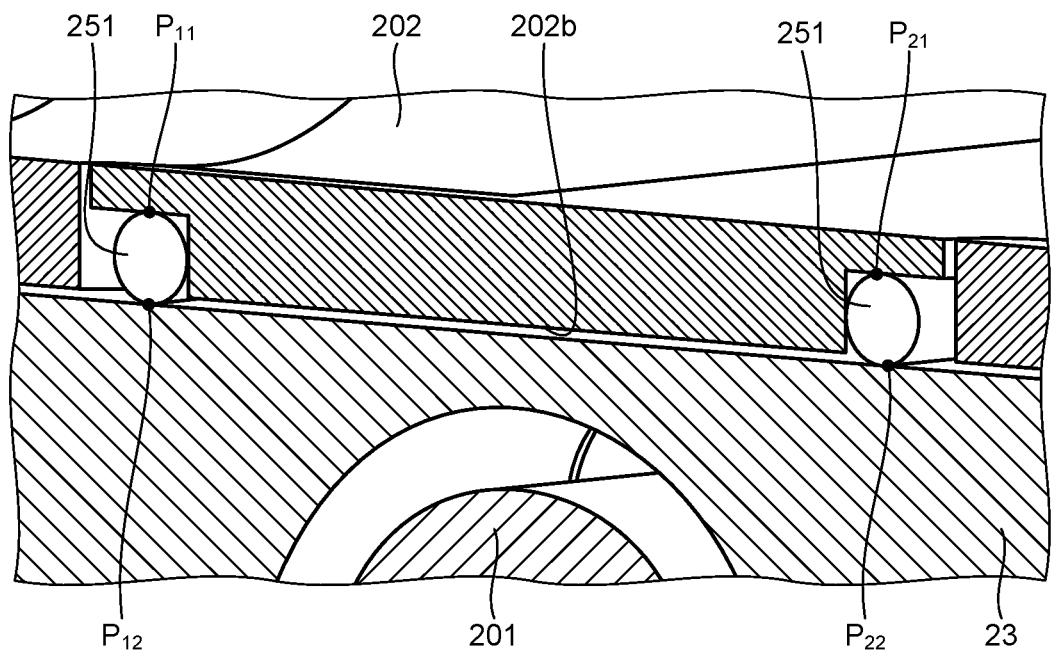
FIG. 30 is an partial enlarged view of the configuration illustrated in FIG. 29.

A thirteenth modification of the embodiment will be described below with reference to FIG. 27 to FIG. 30. FIG. 27 and FIG. 28 are diagrams for explaining a configuration of a main part of a treatment tool according to the thirteenth modification. FIG. 29 is a cross-sectional view for explaining the configuration of the main part of the treatment tool according to the thirteenth modification. FIG. 30 is a partial enlarged view of the configuration illustrated in FIG. 29. Meanwhile, a configuration of a treatment system according to the thirteenth modification is the same as the treatment system 1 as described above except that watertight materials 251 are further provided, and therefore, explanation of the configuration other than the watertight materials 251 will be omitted. A configuration that is different from the embodiment will be described below.

The watertight material 251 is arranged on each of end portions of the second through hole 202b of the sheath 202 (see FIG. 29). The watertight materials 251 have annular shapes (see FIG. 28). The watertight materials 251 come in press-contact with the shaft 23 and the sheath 202, and ensures water-tightness between the shaft 23 and the sheath 202. Specifically, outer peripheral surfaces of the watertight materials 251 and an inner peripheral surface of the sheath 202 come in close contact with each other at positions $P_{11}$ and $P_{21}$. Further, inner peripheral surfaces of the watertight materials 251 and an outer peripheral surface of the shaft 23 come in close contact with each other at positions $P_{12}$ and $P_{22}$. The watertight materials 251 come in close contact with each of the members in a line contact manner or in a plane contact manner.

When manufacturing the treatment tool according to the thirteenth modification, the watertight materials 251 are first arranged on the sheath 202. Thereafter, the same method as the embodiment is performed (see FIG. 6 to FIG. 8).

In the thirteenth modification as described above, the configuration is changed to further include the watertight materials 251 as compared to the embodiment as described above, but a behavior of the treatment tool itself is not changed, so that it is possible to achieve the same effects as the embodiment.

Furthermore, in the thirteenth modification, the watertight materials 251 ensure water-tightness between the shaft 23 and the sheath 202, so that it is possible to prevent intrusion of liquid (for example, body fluid or blood) into the sheath 202.

While the embodiment of the disclosure has been described above, the disclosure is not limited to only the embodiment as described above. The disclosure may include various embodiments and the like that are not described herein. The embodiment and the modifications may be combined appropriately.

Meanwhile, in the embodiment as described above, the examples have been described in which ultrasonic waves or high-frequency power are/is supplied to the probe main body, but it may be possible to adopt a configuration in which only ultrasonic waves are applied without supplying high-frequency power.

Furthermore, in the embodiments as described above, the examples have been described in which the shaft penetrates through the second hole portion of the jaw, but it may be possible to adopt a configuration in which one end of the second hole portion is closed. In this case, the shaft is arranged so as to come into contact with the closed portion of the second hole portion of the jaw.

The ultrasonic treatment tool and the method of manufacturing the ultrasonic treatment tool according to the disclosure as described above are useful to mount a jaw in a rotatable manner while preventing interference between the vibration transmission portion and the jaw with a simple configuration.

According to the disclosure, it is possible to mount a jaw in a rotatable manner while preventing interference between the vibration transmission portion and the jaw with a simple configuration.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment tool that is connected to a transducer unit and that receives ultrasonic waves generated and applied by the transducer unit, the ultrasonic treatment tool comprising:
    a vibration transmission portion configured to vibrate by receiving the applied ultrasonic waves, and transmit vibration to a treatment target;
    a sheath that includes a first through hole in which the vibration transmission portion is inserted while a distal end of the vibration transmission portion is exposed, and a second through hole that has a hole shape penetrating in a different direction from a penetration direction of the first through hole;
    a jaw that includes a first hole portion in which the sheath is inserted and a second hole portion configured to communicate with the second through hole; and
    a shaft that includes a space in which the vibration transmission portion is inserted, and that allows the jaw to rotate relative to the sheath when the shaft is inserted in the second through hole and the second hole portion.

2. The ultrasonic treatment tool according to claim 1, wherein a central axis of the shaft crosses the vibration transmission portion.

3. The ultrasonic treatment tool according to claim 1, wherein the shaft is held by the sheath.

4. The ultrasonic treatment tool according to claim 1, wherein the space in which the vibration transmission portion is inserted is a through hole.

5. The ultrasonic treatment tool according to claim 1, wherein the space in which the vibration transmission portion is inserted has a notch shape.

6. The ultrasonic treatment tool according to claim 1, wherein the second hole portion has a hole shape that extends from mutually-different side portions of the first hole portion.

7. The ultrasonic treatment tool according to claim 1, further comprising:
    a gripped portion connected to the jaw.

8. The ultrasonic treatment tool according to claim 1, further comprising:
    a gripper arranged on a distal end of the jaw, the gripper being configured to grip a target in cooperation with the vibration transmission portion.

9. The ultrasonic treatment tool according to claim 1, wherein high-frequency voltage is supplied to the vibration transmission portion.

10. The ultrasonic treatment tool according to claim 1, further comprising:
    a watertight material that is in close contact with the sheath and the shaft to ensure water-tightness between the sheath and the shaft.

11. The ultrasonic treatment tool according to claim 1, wherein a wall surface forming the space in which the vibration transmission portion is inserted in the shaft has insulating property.

12. A method of manufacturing an ultrasonic treatment tool that is connected to a transducer unit and that receives ultrasonic waves generated and applied by the transducer unit, the method comprising:

- arranging a jaw on a sheath, the sheath including a first through hole in which a vibration transmission portion is inserted while a distal end of the vibration transmission portion is exposed and a second through hole that has a hole shape penetrating in a different direction from a penetration direction of the first through hole, the vibration transmission portion being configured to vibrate by receiving the applied ultrasonic waves and transmit the vibration to a treatment target, the jaw including a first hole portion in which the sheath is inserted and a second hole portion configured to communicate with the second through hole, the jaw being arranged on the sheath such that the sheath is inserted in the first hole portion and the second through hole communicates with the second hole portion;
- inserting a shaft, the shaft including a space in which the vibration transmission portion is inserted, into the second through hole and the second hole portion such that the space is aligned with the penetration direction of the first through hole; and
- inserting the vibration transmission portion into the first through hole and the space of the shaft.

\* \* \* \* \*